(12) United States Patent
Bannen et al.

(10) Patent No.: US 10,184,939 B2
(45) Date of Patent: Jan. 22, 2019

(54) DETECTION OF NEOANTIGENS USING PEPTIDE ARRAYS

(71) Applicant: Roche Sequencing Solutions, Inc., Pleasanton, CA (US)

(72) Inventors: Ryan Bannen, Madison, WI (US); Jigar Patel, Verona, WI (US); Ken Lo, Madison, WI (US)

(73) Assignee: ROCHE SEQUENCING SOLUTIONS, INC., Pleasanton, CA (US)

( * ) Notice: Subject to any disclaimer, the term of this patent is extended or adjusted under 35 U.S.C. 154(b) by 160 days.

(21) Appl. No.: 15/423,768

(22) Filed: Feb. 3, 2017

(65) Prior Publication Data
US 2017/0234868 A1   Aug. 17, 2017

Related U.S. Application Data

(60) Provisional application No. 62/294,771, filed on Feb. 12, 2016.

(51) Int. Cl.
*G01N 33/564*   (2006.01)
*G01N 33/543*   (2006.01)
*G01N 33/574*   (2006.01)
*G01N 33/68*    (2006.01)

(52) U.S. Cl.
CPC ..... *G01N 33/564* (2013.01); *G01N 33/54306* (2013.01); *G01N 33/54386* (2013.01); *G01N 33/574* (2013.01); *G01N 33/6845* (2013.01)

(58) Field of Classification Search
CPC ............................................... G01N 33/54306

USPC .......................................................... 506/9
See application file for complete search history.

(56) References Cited

PUBLICATIONS

Lo K. C. et al, Abstract A156:Anti-p53 auto-antibody serum profiling using high-density peptide arrays, Cancer Immunology Research, (2016), p. A156, vol. 4.
Mock A. et al, Printed peptide arrays identify prognostic TNC serumantibodies in glioblastoma patients, Oncotarget, (2015), pp. 13579-13590, vol. 6.
Rajasagi M. et al, Systematic identification of personal tumor-specific neoantigens in chronic lymphocytic leukemia, Blood, (2014), pp. 453-462, vol. 124, No. 3.

*Primary Examiner* — Karla A Dines
(74) *Attorney, Agent, or Firm* — Daniel Agnew; Eric Grant Lee

(57) ABSTRACT

The present disclosure provides a method of identifying a peptide antigen, including contacting an antibody-comprising composition to a peptide microarray having an array surface and a plurality of feature pairs disposed thereon. Each of the feature pairs includes a first feature of wild-type peptides having a defined sequence and a second feature of mutant peptides having the defined sequence with a single amino acid mutation. Each of the wild-type peptides and the mutant peptides has an array-coupled terminus coupled to the array surface and an opposing free terminus, and the position of the amino acid mutation in the mutant peptides is located closer to the array-coupled terminus of the mutant peptides than the free terminus. The method further includes detecting binding of an antibody in the antibody-comprising composition to at least one of the feature pairs on the peptide microarray, and identifying feature pairs exhibiting differential binding.

20 Claims, 2 Drawing Sheets

Position        18          12    9     6           1
                ↓           ↓     ↓     ↓           ↓
Mutant     N  -  XXXXXXXXXXXX($X_{mu}$)XXXXX  -  C
Wild-type  N  -  XXXXXXXXXXXX($X_{wt}$)XXXXX  -  C

$X_i$ ⟵ 210
[...]
$X_6$
$X_5$
$X_4$    } 204
$X_3$
$X_2$
$X_1$ ⟵ 208
[spacer]
206 ⟶ [6-HA]
                 ⟵ 202

FIG. 3

DETECTION OF NEOANTIGENS USING PEPTIDE ARRAYS

CROSS-REFERENCE TO RELATED APPLICATIONS

This application is based on, claims the benefit of, and hereby incorporates by reference, U.S. Provisional Patent Application Ser. No. 62/294,771 filed 12 Feb. 2016 and entitled, "Detection of Neoantigens Using Peptide Arrays".

STATEMENT REGARDING FEDERALLY SPONSORED RESEARCH

Not applicable.

FIELD OF THE INVENTION

The invention relates to immunology and more specifically, to the use of peptide arrays to detect antibodies to antigens, neoantigens, and autoantibodies.

BACKGROUND OF THE INVENTION

Peptide microarrays are a valuable antibody screening tool. A peptide microarray is able to distinguish antibodies specific to closely related peptides and proteins. For example, somatic mutations produce mutant proteins (neoantigens) which can be recognized by an antibody. A peptide microarray can distinguish an antibody against a neoantigen from an autoantibody specific for a wild-type protein. The latter can potentially be a marker for autoimmune disease.

Autoimmune diseases are characterized by immune responses of an organism against its own cells and tissues. Autoimmune diseases include celiac disease, type I diabetes, systemic lupus erythematosus (SLE), Addison's disease, rheumatoid arthritis, and several others. Autoantibodies—antibodies against a body's own antigens—are the cause of many autoimmune symptoms as well as a diagnostic marker for these conditions. Sensitive detection of autoantibodies is essential for correct and timely diagnosis and symptom management of autoimmune diseases.

Neoantigens are new proteins and peptides resulting from somatic mutations in the genome. Neoantigens are often generated in tumors, including malignant tumors in the course of malignant transformation and tumor progression. These new antigens are a dominant target for tumor-infiltrating lymphocytes (TILs). Identifying these antigens and antibodies specific to them holds potential for personalized cancer immunotherapy. Therapeutic vaccination with neoantigens has been shown to produce anti-tumor immune response (Senci, M., et al., 2006. *Unique tumor antigens: evidence for immune control of genome integrity and immunogenic targets for T-cell mediated patient-specific immunotherapy*. Clin. Cancer Res. 12:5023).

One way of identifying neoantigens is whole-genome exome sequencing to reveal mutated coding sequences. Computational analysis is then used to determine which of the mutated peptides will be good antigens, i.e., are likely to fit into the cleft of the patient-specific HLA Class I molecule (Hacohen, N., et al., 2013. *Getting personal with neoantigen-based therapeutic cancer vaccine* Cancer Immunology Research 1:11). One study was able to validate that neoantigens are immunogenic by exposing CD8+ T-cells from the patient to antigen-presenting cells (APC) pulsed with a mixture of in vitro synthesized neo-antigen peptides and then testing for T-cell activation (Rajasagi M., et aL, 2014. *Systematic identification of personal tumor-specific neoantigens in chronic lymphocytic leukemia*, Blood 124:453). In this emerging field of cancer therapy, there is a need to quickly and reliably identify which tumor-specific peptides are immunogenic and have therapeutic potential.

Screening serum antibodies using peptide microarrays provides valuable diagnostic information about the subject. More generally, a peptide microarray can characterize antibodies in a polyclonal serum or one or more isolated antibodies with respect to their antigens. There is a need for a reliable system of interrogating antibody specificity by presenting multiple variations of the same peptide sequence.

SUMMARY OF THE INVENTION

In one embodiment, the invention is a method of identifying a neoantigen in a subject comprising contacting an antibody-comprising composition derived from a subject to a microarray having addressable features, wherein each feature comprises a wild-type or a mutant peptide and the mutant position in the mutant peptide is placed near the C-terminus of the peptide, detecting binding of an antibody to one or more features on a microarray, identifying features containing a mutant peptide where the binding has occurred while the binding has not occurred in features containing a corresponding wild-type peptide, detecting the identified mutant peptides as neoantigens. The antibody-comprising composition can be a blood serum. The mutant position in the mutant peptide can be placed 5 amino acids away from the C-terminus.

In another embodiment, the invention is a method of identifying an antibody specific to a neoantigen in a subject comprising contacting an antibody-comprising composition derived from a subject to a microarray having addressable features, wherein each feature comprises a wild-type or a mutant peptide and the mutant position in the mutant peptide is placed near the C-terminus of the peptide, detecting binding of an antibody to one or more features on a microarray, identifying features containing a mutant peptide where the binding has occurred while the binding has not occurred in features containing a corresponding wild-type peptide, identifying antibodies binding to said identified features as anti-neoantigen antibodies.

In another embodiment, the invention is a method of detecting autoantibodies in a subject comprising contacting an antibody-comprising composition derived from a subject to a microarray having addressable features, wherein each feature comprises a wild-type or a mutant peptide and the mutant position in the mutant peptide is placed near the C-terminus of the peptide, detecting binding of an antibody to one or more features on a microarray, identifying features containing a wild-type peptide where the binding has occurred while the binding has not occurred in any of the features containing corresponding mutant peptides, identifying antibodies binding to said identified features as autoantibodies. The method can further comprise diagnosing autoimmune disease in the subject.

In another embodiment, the invention is a microarray for identifying neoantigens or autoantibodies in a subject comprising addressable features, wherein each feature comprises a wild-type or a mutant peptide and the mutant position in the mutant peptide is placed near the N-terminus of the peptide. The mutant position can be 5 amino acids away from the C-terminus of the peptide.

In yet another embodiment, the invention is a system for identifying neoantigens or autoantibodies in a subject comprising a microarray with addressable features, wherein each feature comprises a wild-type or a mutant peptide and the mutant position in the mutant peptide is placed near the C-terminus of the peptide, and a detection reagent generating a detectable signal when an antibody binds to a feature in the microarray. The system may further comprise means of computation to compare the detectable signals from features with mutant and wild-type peptides.

In one embodiment, the present disclosure provides a method of identifying a peptide antigen including contacting an antibody-comprising composition derived from a subject to a peptide microarray having an array surface and a plurality of feature pairs disposed thereon. Each of the feature pairs includes a first feature of wild-type peptides having a defined sequence and a second feature of mutant peptides having the defined sequence with a single amino acid mutation. Each of the wild-type peptides and the mutant peptides has an array-coupled terminus coupled to the array surface and an opposing free terminus, and the position of the amino acid mutation in the mutant peptides is located closer to the array-coupled terminus of the mutant peptides than the free terminus. The method further includes detecting binding of an antibody in the antibody-comprising composition to at least one of the plurality of feature pairs on the peptide microarray, and identifying feature pairs exhibiting differential binding.

In one aspect, the position of the amino acid mutation in the mutant peptides is located within the first 9 amino acid positions numbered from the array-coupled terminus of the mutant peptides.

In another aspect, the position of the amino acid mutation in the mutant peptides is located at amino acid position 6 numbered from the array-coupled terminus of the mutant peptides.

In yet another aspect, the array-coupled terminus of the mutant peptides is the C-terminus.

In still another aspect, the single amino acid mutation is selected from one of a substitution, a modification, a deletion, and an insertion.

In a further aspect, each of the array-coupled termini is coupled to the array surface via at least one of a linker and a spacer.

In one aspect, the spacer includes at least one amino acid selected from glycine and serine.

In another aspect, the linker includes at least one 6-hexanoic acid molecule.

In another aspect, each of the wild-type peptides and the mutant peptides has a length of at least 12 amino acids.

In yet another aspect, each of the wild-type peptides and the mutant peptides has a length of at least 16 amino acids.

In still another aspect, the method further includes characterizing the mutant peptides identified as exhibiting differential binding as neoantigens.

In one aspect, the method further includes diagnosing autoimmune disease in the subject.

In another aspect, the antibody-comprising composition is a blood serum composition.

According to another embodiment, a method of identifying a peptide antigen includes contacting an antibody-comprising composition derived from a subject to a peptide microarray having an array surface and a plurality of feature pairs disposed thereon. Each of the feature pairs includes a first feature of wild-type peptides having a defined sequence and a second feature of mutant peptides having the defined sequence with a single amino acid mutation. Each of the wild-type peptides and the mutant peptides is coupled to the array surface via the C-terminus of each of the peptides, and the position of the amino acid mutation in the mutant peptides is located within the first 6 amino acid positions numbered from the C-terminus of the mutant peptides. In addition, each of the wild-type peptides and the mutant peptides has a length of at least 16 amino acids. The method further includes detecting binding of an antibody in the antibody-comprising composition to at least one of the plurality of feature pairs on the peptide microarray, identifying feature pairs exhibiting differential binding, and characterizing the mutant peptides of the feature pairs identified as exhibiting differential binding as neoantigens.

In one aspect, the antibody-comprising composition is a blood serum composition.

According to yet another embodiment, a system for identifying a peptide antigen includes a peptide microarray having an array surface and a plurality of feature pairs disposed thereon. Each of the feature pairs includes a first feature of wild-type peptides having a defined sequence and a second feature of mutant peptides having the defined sequence with a single amino acid mutation. Each of the wild-type peptides and the mutant peptides has an array-coupled terminus coupled to the array surface and an opposing free terminus, and the position of the amino acid mutation in the mutant peptides is located closer to the array-coupled terminus of the mutant peptides than the free terminus. The system further includes a detector for detecting binding of an antibody in the antibody-comprising composition to at least one of the plurality of feature pairs on the peptide microarray.

In one aspect, the position of the amino acid mutation in the mutant peptides is located within the first 6 amino acid positions relative to the array-coupled terminus of the mutant peptides.

In another aspect, each of the array-coupled termini is coupled to the array surface via at least one of a linker and a spacer.

In yet another aspect, each of the wild-type peptides and the mutant peptides has a length of at least 12 amino acids.

According to still another embodiment, a peptide microarray for identifying a peptide antigen includes an array surface, and a plurality of feature pairs disposed thereon. Each of the feature pairs includes a first feature of wild-type peptides having a defined sequence, and a second feature of mutant peptides having the defined sequence with a single amino acid mutation. Each of the wild-type peptides and the mutant peptides has an array-coupled terminus coupled to the array surface and an opposing free terminus, the position of the amino acid mutation in the mutant peptides is located closer to the array-coupled terminus of the mutant peptides than the free terminus, and each of the wild-type peptides and the mutant peptides has a length of at least 12 amino acids.

In one aspect, the position of the amino acid mutation in the mutant peptides is located within the first 6 amino acid positions relative to the array-coupled terminus of the mutant peptides.

BRIEF DESCRIPTION OF THE DRAWINGS

FIG. 2 is an illustration of amino acid sequences for mutant and wild-type peptide features with amino acid sequence positions 1, 6, 9, 12, and 18 indicated relative to the C-terminus. The mutation in the mutant peptide feature is indicated as ($X_{mu}$) at position 6 relative to the C-terminus, and the corresponding amino acid position in the wild-type peptide feature is indicated as ($X_{wt}$). The N-terminus (free end of the peptide) and the C-terminus (array-coupled end of the peptide) are indicated as "N" and "C", respectively.

FIG. 3 is an illustration of a portion of a peptide microarray showing a single peptide feature in isolation. The peptide feature includes at least one peptide coupled to the array surface via a spacer and a 6-hexanoic acid (6-HA) linker. The amino acids defining the sequence of the peptide are number from position 1 ($X_1$) at the array-coupled terminus through position i ($X_i$) at the opposing free terminus of the peptides.

DETAILED DESCRIPTION OF THE INVENTION

Definitions

Figure 1:
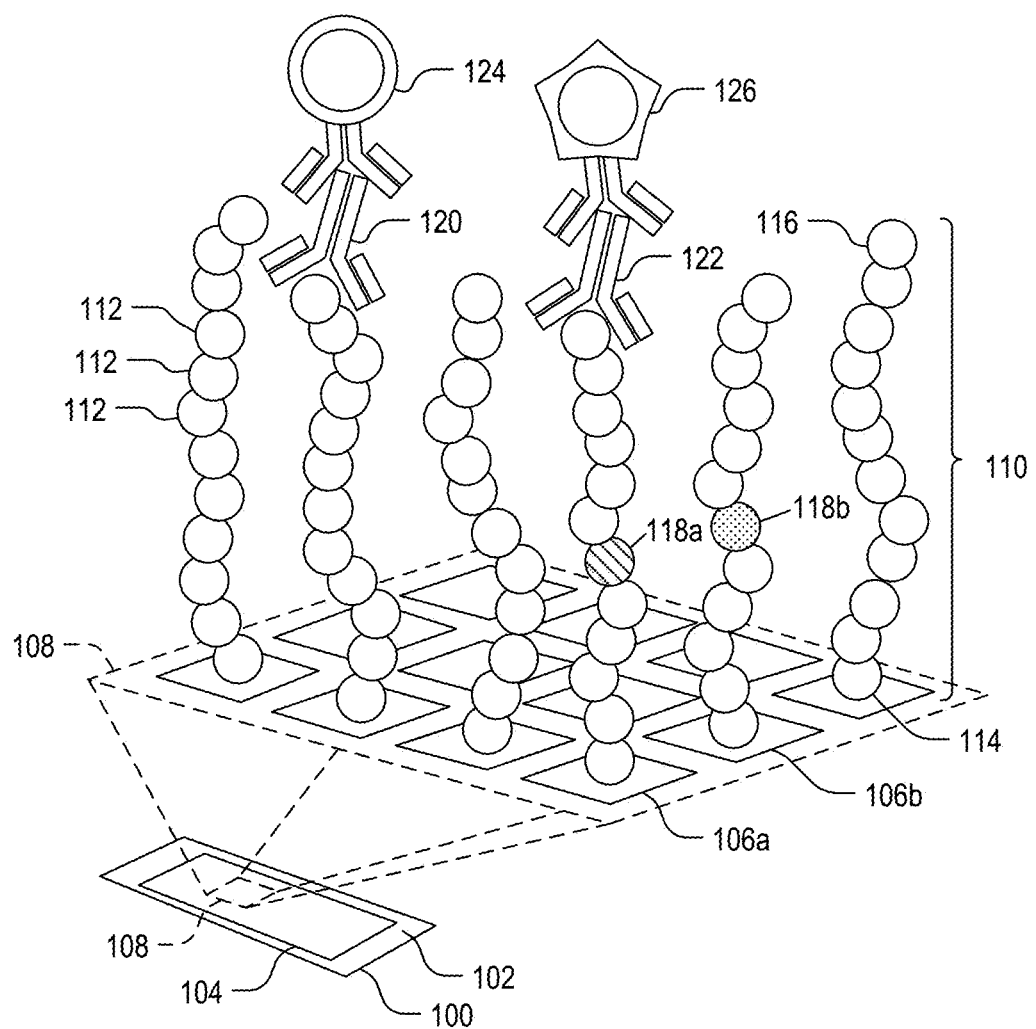
FIG. 1 is a schematic illustration of an embodiment peptide microarray including a plurality of peptide features bound by primary and secondary antibodies according to the present disclosure.

As used herein, the terms "peptide" and "oligopeptide" refer to organic compounds composed of amino acids, which may be arranged in either a linear or cyclic chain of amino acids joined together by peptide bonds between the carboxyl and amino groups of adjacent residues. The terms "peptide" and "oligopeptide" refer to shorter polypeptides, i.e., organic compounds composed of less than 50 amino acid residues.

The term "natural amino acid" refers to one of the 20 amino acids encoded by the standard genetic code and typically found in proteins and used for protein biosynthesis as well as other amino acids which can be incorporated into proteins during translation (including pyrrolysine and selenocysteine). The 20 natural amino acids include histidine, alanine, valine, glycine, leucine, isoleucine, aspartic acid, glutamic acid, serine, glutamine, asparagine, threonine, arginine, proline, phenylalanine, tyrosine, tryptophan, cysteine, methionine, and lysine.

The term "non-natural amino acid" refers to an organic compound that is not among those encoded by the standard genetic code, or incorporated into proteins during translation. The non-natural amino acids include amino acids or analogs of amino acids, for example, the D-isostereomers of amino acids (D-amino acids), the beta-amino-analogs of amino acids, citrulline, homocitrulline, homoarginine, hydroxyproline, homoproline, ornithine, 4-amino-phenylalanine, cyclohexylalanine, α-aminoisobutyric acid, N-methyl-alanine, N-methyl-glycine, norleucine, N-methyl-glutamic acid, tert-butylglycine, α-aminobutyric acid, tert-butylalanine, 2-aminoisobutyric acid, α-aminoisobutyric acid, 2-aminoindane-2-carboxylic acid, selenomethionine, dehydroalanine, lanthionine, γ-amino butyric acid, and derivatives thereof wherein the amine nitrogen has been mono- or di-alkylated.

The terms "microarray", "peptide microarray", "peptide array", or simply "array" refer to a two-dimensional arrangement of features (oligopeptides) on the surface of a solid or semi-solid support. A single microarray or, in some cases, multiple microarrays (e.g., 3, 4, 5, or more microarrays) can be located on one solid support. The size of the microarrays depends on the number of microarrays on one solid support. The higher the number of microarrays per solid support, the smaller the arrays have to be to fit on the solid support. The arrays can be designed in any shape, but preferably they are designed as squares or rectangles. The ready to use product is the oligopeptide microarray on the solid or semi-solid support referred to as a "microarray slide".

The term "feature" refers to a defined area on the surface of a microarray. The feature comprises biomolecules, such as in the context of the present invention, peptides. One feature can contain biomolecules with different properties, such as different sequences or orientations, as compared to other features. The size of a feature is determined by two factors: i) the number of features on an array (the higher the number of features on an array, the smaller is each single feature); and ii) the number of individually addressable aluminum mirror elements which are used for the irradiation of one feature. The higher the number of mirror elements used for the irradiation of one feature, the bigger is each single feature. The number of features on an array may be limited by the number of mirror elements (pixels) present in the micro mirror device. For example, the state of the art micro mirror device from Texas Instruments, Inc. currently contains 4.2 million mirror elements (pixels), thus the number of features within such exemplary microarray is therefore limited by this number. However, it should be understood that the micro mirror device from Texas Instruments, Inc. is provided only for exemplary purposes and higher density arrays are or will become available.

The term "solid or semi-solid support" refers to any solid material, having a surface area to which organic molecules can be attached through bond formation or absorbed through electronic or static interactions such as covalent bond or complex formation through a specific functional group. The support can be a combination of materials such as plastic on glass, carbon on glass, and the like. The functional surface can be simple organic molecules but can also comprise of co-polymers, dendrimers, molecular brushes, and the like.

The term "wild-type peptide" refers to a peptide that is a portion of the protein and has the amino acid sequence of the wild-type (unmutated) protein such as found for example in a reference database (e.g., UNIPROT).

The term "mutant peptide" refers to a peptide that is a portion of the protein and has the sequence that differs from the wild-type sequence by one amino acid. A single amino acid change in a protein may be represented in multiple mutant peptides depending on the placement of the mutant amino acid within the peptide.

The terms "wild-type peptide and corresponding mutant peptide" and "mutant peptide and corresponding wild-type peptide" refer to a pair of peptides where in one is wild-type and the other differs from that wild-type peptide by at least one amino acid. Each mutant peptide typically has only one corresponding wild-type peptide but each wild-type peptide may have several corresponding mutant peptides.

The present invention relates to a method of making and using a peptide microarray containing wild-type and mutant peptide sequences. A mutant protein comprising the mutant peptide sequence may result from a point mutation creating a single nucleotide polymorphism (SNP) in the coding region of the gene encoding the protein. A serum from a subject may contain antibodies to wild-type proteins (autoantibodies) as well as antibodies to mutant proteins (neoantigens). In some embodiments, screening the microarray with a serum may reveal the presence of autoantibodies (possibly indicative of autoimmune disease). In other embodiments, screening the microarray with a serum may reveal the presence of neoantigens (possibly indicative of a tumor or mismatch repair deficiency).

The inventors discovered that the ability of an antibody to distinguish between two peptides differing by a single amino acid is position-dependent. The inventors discovered that in the context of a microarray, the ability to detect a single amino acid difference is dramatically improved when the mutant amino acid is positioned closer to the array-coupled terminus of the peptide.

Methods of forming a peptide microarray are known in the art. Certain methods of producing peptide arrays comprise spotting prefabricated peptides or in-situ synthesis by spotting reagents on membranes see U.S. Pat. No. 6,375,903. Other known methods used for generating peptide arrays of higher density involve photolithographic techniques, where the synthetic design of the desired biopolymers is controlled by suitable photolabile protecting groups (PLPG) releasing the linkage site for the respective next amino acid upon exposure to electromagnetic radiation, such as light (Fodor et al., (1993) *Nature* 364:555-556; Fodor et al., (1991) *Science* 251:767-773). Two different photolithographic techniques are known in the art. The first is a photolithographic mask used to direct light to specific areas of the synthesis surface effecting localized deprotection of the PLPG. These "masked" methods include the synthesis of polymers utilizing a mount ("mask") which engages a substrate and provides a reactor space between the substrate and the mount. See U.S. Pat. Nos. 5,143,854 and 5,445,934. The second photolithographic technique is the so-called maskless photo-lithography, where light is directed to specific areas of the synthesis surface effecting localized deprotection of the PLPG by digital projection technologies, such as micromirror devices (Singh-Gasson et al., *Nature Biotechn.* 17 (1999) 974-978). Such "maskless" array synthesis eliminates the need for time-consuming and expensive production of exposure masks. The peptide microarrays utilized in the method of the present invention may be synthesized by any of the methods described above or any other methods known in the art including the method previously described by the inventors in U.S. application Ser. No. 14/577,334 *Systemic Discovery, Maturation and Extension of Peptide Binders to Proteins* filed on Dec. 19, 2014.

In some embodiments, the method of the invention involves the use of an array of peptide features on a solid support, each feature having the structure illustrated in FIG. 1. As shown in FIG. 1, each feature comprises a peptide sequence linked to the solid support at a terminus of the peptide sequence. The peptide sequences on the microarray are mutant and wild-type. FIG. 2 illustrates a mutant/wild-type sequence pair where the mutation is placed at position 6. (The numbering of amino acids begins at the C-terminus). Several mutant sequences may correspond to a single wild-type sequence. In some embodiments, one or more mutant sequences are placed in the vicinity of the corresponding wild-type sequence on the microarray. The mutant position in each mutant peptide is placed near the array-coupled terminus of the peptide, preferably within the first 6 amino acids numbered from the array-coupled terminus.

Within the microarray feature, the peptides are about 12-20 amino acids long. In some embodiments, the peptides on the array are synthesized using only natural amino acids encoded by the standard genetic code. Non-natural amino acids may also be used. All 20, or fewer than 20 (e.g., only 18 natural amino acids) can be used. In some embodiments, the array is synthesized using 18 natural amino acids and not including cysteine (Cys) and methionine (Met). In yet other embodiments, the peptide sequences on the array further exclude any dimer or a longer repeat of the same amino acid.

For maskless array-based synthesis, the number of features that can be synthesized on a given peptide array depends in part on the number of individual mirrors provided on the micromirror device. In one example, a peptide array can contain up to $2.9 \times 10^6$ features having up to $10^7$ reactive sites that could yield a full length peptide. Smaller or larger arrays can also be designed. For example, an array representing a comprehensive list of all possible 5-mer peptides using all natural amino acids excluding cysteine will have 2,476,099 ($\sim 2.5 \times 10^6$) peptides. An array excluding certain amino acids and amino acid dimers can currently have about 1M ($10^6$) peptides. Further, it will be appreciated that arrays can be synthesized using alternative or additional synthesis techniques, such as mask-based array and spotted or printed array synthesis.

Binding of an antibody to one or more peptides on the microarray may be detected by methods known in the art. For example, a reporter-conjugated secondary antibody (e.g., anti-IgG for the appropriate organism) may be used. Commercial anti-IgG antibodies conjugated to reporter molecules are available.

In some embodiments, the invention is a method of identifying one or more neoantigens in a subject using a peptide microarray. The method comprises a step of contacting one or more antibodies from a subject (e.g., a serum or composition comprising one or more isolated antibodies) to a microarray having addressable features, wherein each feature comprises a wild-type or a mutant peptide (neoantigen). The mutant position in the neoantigen is placed near the C-terminus of the peptide, preferably 5 amino acids away from the C-terminus. The method further comprises comparing the signals from the neoantigens and wild-type peptides to verify that one or more antibodies from the subject are specific to the neoantigen and the neoantigen is likely present in the subject.

In some embodiments, the invention is a method of identifying one or more antibodies specific to neoantigens in a subject using a peptide microarray. The method comprises a step of contacting one or more antibodies from a subject (e.g., a serum or composition comprising one or more isolated antibodies) to a microarray having addressable features, wherein each feature comprises a wild-type or a mutant peptide (neoantigen). The mutant position in the neoantigen is placed near the array-coupled terminus of the peptide, preferably within the first 6 amino acid positions numbered from the array-coupled terminus. The method further comprises comparing the signals from the neoantigens and wild-type peptides to verify that one or more antibodies from the subject are specific to the neoantigen and identifying the anti-neoantigen antibodies.

In some embodiments, the invention is a method of detecting autoantibodies in a subject using a peptide microarray. The method comprises a step of contacting one or more antibodies from a subject (e.g., a serum or composition comprising one or more isolated antibodies) to a microarray having addressable features, wherein each feature comprises a wild-type or a mutant peptide (neoantigen). The mutant position in the neoantigen is placed near the array-coupled terminus of the peptide, preferably within the first 6 amino acid positions numbered from the array-coupled terminus. The method further comprises comparing the signals from the neoantigens and wild-type peptides to verify that one or more antibodies from the subject are specific to wild-type peptides and autoantibodies are likely present in the subject. In some embodiments, the method further comprises diagnosing autoimmune disease in the subject.

In some embodiments, the invention is a microarray for identifying neoantigens or autoantibodies in a subject. The microarray comprises addressable features, wherein each feature comprises a wild-type or a mutant peptide (neoantigen). The mutant position in the neoantigen is placed near the array-coupled terminus of the peptide, preferably within the first 6 amino acids positions numbered from the array-coupled terminus. In some embodiments, the invention is a system for identifying neoantigens or autoantibodies. The system comprises the microarray described above and method of detecting antibodies bound to the microarray, such as a secondary antibody and a reporter molecule. The system may also comprise computational means of identifying autoantibodies or neoantigens. Detection may involve a step of comparing binding to the wild-type peptide and a corresponding mutant peptide. The computational means are capable of correlation of the signal and the corresponding peptide sequence on the microarray to identify the sequence of the neoantigen. In some embodiments, the system further comprises reporting means for reporting the neoantigen sequences.

The invention is based on the surprising discovery that for optimal discrimination by an antibody, the mutant residue must be placed closer to the array-coupled terminus (bound to solid support) and not closer to the free terminus that is facing the antibody-containing solution and opposing the array-coupled terminus. The unexpected results shown in the examples below enabled the inventors to create the novel methods and compositions described herein.

Turning now to FIG. 1, a peptide microarray 100 for identifying a peptide antigen includes an array surface 102. A portion 104 of the array surface 102 defines an area in which a plurality of peptide features 106 are disposed on the array surface 102. An enlarged view of the subsection 108 of the portion 104 illustrates that each of the features 106 defines an area on the array surface 102 on which a plurality of peptides 110 are synthesized. The peptides 110 are synthesized using any suitable synthesis method. In one example, peptides are synthesized using maskless photolithography, where light is directed to specific areas of the synthesis surface effecting localized deprotection of photolabile protecting groups by digital projection technologies, such as micro mirror devices (see, e.g., Singh-Gasson et al., Nature Biotechn. 17 (1999) 974-978, and U.S. Pat. No. 8,658,572 to Albert et al. filed 13 Mar. 2012). It will be appreciated that while each feature 106 is illustrated as including a single peptide 110, a feature 106 can include a large number of peptides 110, with each of the peptides 110 in a given feature 106 synthesized to have the identical sequence. Moreover, while a particular feature 106 includes peptides 110 having the same sequence, different features 106 can have peptides 110 with different sequences. Accordingly, a first feature 106a can have peptides 110 with a first sequence, and a second feature 106b can have peptides 110 with a second sequence different from the first sequence.

With continued reference to FIG. 1, the sequence of each of the peptides 110 is determined by the order and identity of the one or more amino acids 112 that make up each of the peptides 110. In the present example, the peptides 110 are illustrated as having a length of 12 amino acids 112. However, a peptide 110 can include any number of amino acids 112 subject to the limits of the particular synthesis technology. In one example, each of the peptides 110 includes at least 12 amino acids. In another example, each of the peptides 110 includes at least 16 amino acids. In yet another example, each of the peptides 110 includes exactly 18 amino acids.

Each of the peptides 110 further includes an array-coupled terminus 114 and a free terminus 116. The array-coupled terminus 114 can be either of the amino-terminus (i.e., N-terminus) or the carboxyl-terminus (i.e., C-terminus) of a peptide 110 depending on the selected synthesis approach. Generally, each of the peptides 110 are coupled to the array surface 102 via the same terminus (i.e., either the N-terminus or the C-terminus). In the case that the array-coupled terminus is the C-terminus of each of the peptides 110, the peptides 110 are coupled to the array surface 102 via the amino acid 112 present at the C-terminus of each of the peptides 110. In general, the coupling is achieved through the C-terminal carboxyl group of the peptide 110, and can further include one or more additional linker or spacer molecules (see FIG. 3) intermediate the array surface and the peptide 110. However, the peptides 110 can alternatively (or additionally) be coupled to the array surface 102 via other side-chains or reactive groups included in the peptides 110 (see e.g., U.S. patent application Ser. No. 15/136,028 to Patel et al. filed 22 Apr. 2016). In one aspect, the linker includes one or more 6-hexanoic acid molecules. In another aspect, the spacer includes one or more amino acids (e.g., a series of three amino acids selected from glycine and serine).

As described above, the array-coupled terminus 114 is coupled to the array surface 102. In this configuration, the amino acids 112 in the peptides 110 can be numbered starting from position 1 at the array-coupled terminus 114 and ending with position "i" at the free terminus 116, where "i" is the total number of amino acids 112 in the particular peptide 110. In the present example, amino acids 118a and 118b are at amino acid position 6 as numbered from the array-coupled terminus 114 of the peptides 110.

In some embodiments, it may be useful to provide for pairs of peptide features 106 on the microarray 100. For example, pairs of wild-type and mutant peptide features can be used for the identification of neoantigens as described herein. Each pair of features 106 includes a first feature 106a of wild-type peptides and a second feature 106b of mutant peptides. The wild-type peptides have a defined sequence of amino acids 112, whereas the mutant peptides have the same defined sequence as the wild-type peptides with the exception that the sequence of the mutant peptides includes a single amino acid mutation (e.g., an amino acid substitution, insertion, modification, deletion, or the like) relative to the wild-type peptides. In the example illustrated in FIG. 1, a first feature 106a includes peptides 110 having a defined sequence including the wild-type amino acid 118a in the 6th position as numbered from the array-coupled terminus 114 of the peptides 110 in the feature 106a. By comparison, the second feature 106b includes peptides 110 having the same defined sequence as the peptides 110 in the feature 106a, with the exception that the peptides 110 in the feature 106b include a mutant amino acid 118b in the sixth position as numbered from the array-coupled terminus 114 of the peptides 110 in the feature 106b. That is, the feature 106a and the feature 106b are considered a feature pair for the reason that the peptides 110 in feature 106a have the same amino acid sequence as the peptides 110 in the feature 106b with the exception of a single amino acid mutation at the 6th position of each of the peptides 110 in the feature 106b relative to the peptide 110 in the feature 106a.

In example, if the amino acid 118a is an alanine in the wild-type peptides 110 in the feature 106a, the amino acid 118b can be a histidine in the mutant peptides 110 in the feature 106b. In another example, if the amino acid 118a is an arginine in the wild-type peptides 110 in the feature 106a, the amino acid 118b can be a citrulline in the mutant peptides 110 in the feature 106b. It will be appreciated that yet other amino acid mutations can be made.

As shown in FIG. 1, the peptides 110 can be detected using, among other techniques, labeled antibodies. In the illustrated embodiment, a first primary antibody 120 and a second primary antibody 122 are contacted to the microarray 100 at which point each of the primary antibody 120 and the primary antibody 122 are bound to a corresponding epitope present within one or more of the peptides 110. For example, the primary antibody 122 may be known to interact with an epitope including the amino acid 118a in the peptides 110 within the feature 106a. In one aspect, the primary antibody 120 and the primary antibody 122 can be present in an antibody-comprising composition derived from a subject, such as a blood-serum composition. In another aspect, the primary antibody 122 (and/or primary antibody 120) can exhibit differential affinity for binding to epitopes present in wild-type peptides and mutant peptides in respective features of a feature pair (e.g., feature 106a and feature 106b).

Subsequent to contacting the microarray 100 with one or more primary antibodies, the microarray 100 can be contacted with a composition comprising one or more secondary antibodies such as the labeled secondary antibody 124 and the labeled secondary antibody 126. The labeled secondary antibody 124 and the labeled secondary antibody 126 can have different labels. For example, the labeled secondary antibody 124 can have a Cy3 label and the labeled secondary antibody 126 can have a Cy5 label. The labeled secondary antibody 124 and the labeled secondary antibody 126 bind to or otherwise interact with the primary antibodies (e.g., the first primary antibody 120 and the second primary antibody 122) to enable the identification of which of the features 106 were bound by the primary antibodies (e.g., primary antibody 120 and primary antibody 122). In one aspect the microarray 100 can be scanned with a detector capable of visualizing which of the features 106 are labeled with the secondary antibody 124 and the secondary antibody 126. In general, this approach enables the detection of binding of a primary antibody in an antibody-comprising composition to feature pairs on the peptide microarray, and subsequent identification of feature pairs exhibiting differential binding to the primary antibodies. In one aspect, the mutant peptides identified through such a differential binding experiment can be characterized as neoantigens.

Turning now to FIG. 2, an example of a wild-type peptide is shown as having a defined sequence of 18 amino acids. Although each of the amino acids is represented by an "X", it will be appreciated that the wild-type peptide can have any defined sequence where each X represents a particular amino acid. FIG. 2 further illustrates a mutant peptide as having the same defined sequence as the wild-type peptide with the exception of a single amino acid mutation at the 6th position (i.e., $X_{mu}$ vs. $X_{wt}$) as numbered from the C-terminus. Each of the wild-type and mutant peptides can be synthesized as distinct features on a peptide microarray. In one example, the peptides are synthesized using light-directed, maskless array synthesis in the direction from the C-terminus to the N-terminus. In this case, the C-terminus is the array-coupled terminus, and the position of the single amino acid mutation ($X_{mu}$) in the mutant peptide is located near the array-coupled terminus of the mutant peptide.

As described herein, the surprising discovery has been made that placement of the polymorphic (i.e., wild-type vs. mutant) amino acid can affect the detection sensitivity of an antibody that preferentially binds the mutant sequence over the wild-type sequence. Whereas existing solutions place the polymorphism in the center of the peptide, the present disclosure provides for a system and method for placement of the polymorphism to achieve greater discrimination (defined herein as the difference between the signal derived from the mutant peptide and signal derived from the wild type peptide). Surprisingly, by placing the polymorphism closer to the array-bound terminus of the peptide being interrogated, the resulting measures of discrimination and reproducibility were substantially better.

In one aspect, the pair of wild-type and mutant peptides is synthesized such that the single amino acid mutation or polymorphism is located closer to the array-bound terminus than the free terminus of the peptides. In another aspect, the pair of wild-type and mutant peptides is synthesized such that the single amino acid mutation or polymorphism is located within the first 12 amino acid positions as numbered from the array-coupled terminus of the mutant peptides. In another aspect, the pair of wild-type and mutant peptides is synthesized such that the single amino acid mutation or polymorphism is located within the first 9 amino acid positions as numbered from the array-coupled terminus of the mutant peptides. In still another aspect, the pair of wild-type and mutant peptides is synthesized such that the single amino acid mutation or polymorphism is located within the first 6 amino acid positions as numbered from the array-coupled terminus of the mutant peptides. In a further aspect, the pair of wild-type and mutant peptides is synthesized such that the single amino acid mutation or polymorphism is located at the 6th amino acid position as numbered from the array-coupled terminus of the mutant peptides.

Referring now to FIG. 3, another example of a single feature 200 on a portion of a larger peptide microarray 202 includes a peptide 204 coupled to an array surface 206. The peptide 204 includes an array-coupled terminus 208, a free terminus 210 opposing the array-coupled terminus 208, and a sequence of amino acids ($X_1, X_2, \ldots, X_i$). In the present illustration, $X_1$ represents the amino acid in the $1^{st}$ position numbered from the array-coupled terminus 208 of the peptide 204, and $X_i$ represents the amino acid in the $i^{th}$ position numbered from the array coupled terminus 208 of the peptide 204, where i is the total number of amino acids in the peptide 204. In one aspect, the amino acid $X_1$ is coupled to the array surface 206 via both a spacer and a 6-hexanoic acid (6-HA) linker. One example of a spacer includes a series of three amino acids selected from glycine and serine. However, additional or alternative spacers and linkers can be used to couple the peptide 204 to the peptide microarray 202.

EXAMPLES

Example 1. Testing Sera from Colorectal Cancer (CRC) Patients

Six serum samples were bound to an array design to determine the optimal position for the detection of antibodies against neoantigens. Three of the serum samples were obtained from colorectal cancer patients and were previously characterized by ELISA to contain autoantibodies against p53. The labels "low", "med", and "high" corresponded to the level of autoantibodies found by ELISA. The other three samples were obtained from healthy individuals. Both "control" and "ISD" were serum samples derived from single donors. "MPS" was a pooled serum sample from multiple healthy individuals. With reference to FIG. 2, peptide probes were synthesized for each wild-type/mutant pair such that the single amino acid change occurred at either position 6, 9, or 12 of an 18-mer peptide numbered relative to the array-bound terminus of the peptide (i.e., the C-terminus in the case of the present example). Following array synthesis, the serum samples (including the primary antibodies) were contacted to the arrays to enable binding of peptides by the antibodies. Thereafter, the arrays were contacted with a composition included labeled secondary antibodies for detection of the primary antibodies, and subsequent identification of feature pairs exhibiting differential binding.

Reproducibility

To assess detection reproducibility, we calculated the Pearson's correlation coefficients of the discrimination between 3 technical replicates. Discrimination is defined as the difference in the log transformed signal between the mutant and wild-type peptide. The mean Pearson's correlation of all pairwise comparison (i.e., replicate 1 vs. replicate 2, replicate 2 vs. replicate 3, and replicate 1 vs. replicate 3) were reported for each mutational position. In addition, Pearson's correlation coefficients were calculated both for mean discrimination (Table 1) and raw discrimination (Table 2).

TABLE 1

Pearson's correlation coefficients of discrimination means between replicates demarcated by the mutation position

| mutation position (#'d from C-terminus) | Pearson's Correlation Coefficients for discrimination means | | | | | |
|---|---|---|---|---|---|---|
| | low | med | high | control | ISD | MPS |
| 6 | 0.953 | 0.927 | 0.956 | 0.916 | 0.945 | 0.954 |
| 9 | 0.951 | 0.916 | 0.954 | 0.907 | 0.944 | 0.950 |
| 12 | 0.942 | 0.904 | 0.958 | 0.915 | 0.927 | 0.942 |

TABLE 2

Pearson's correlation coefficients of raw discrimination between technical replicates demarcated by the mutation position

| mutation position (#'d from C-terminus) | Pearson's Correlation Coefficients for raw discrimination | | | | | |
|---|---|---|---|---|---|---|
| | low | med | high | control | ISD | MPS |
| 6 | 0.851 | 0.752 | 0.837 | 0.756 | 0.798 | 0.839 |
| 9 | 0.834 | 0.723 | 0.831 | 0.737 | 0.797 | 0.818 |
| 12 | 0.803 | 0.684 | 0.836 | 0.723 | 0.753 | 0.787 |

As can been seen in Tables 1 and 2, placing the mutation in position 6 relative to the C-terminus of an 18-mer peptide yielded the highest Pearson's correlation coefficient when comparing the raw discrimination values and discrimination means between technical replicates. Collectively, by placing the mutation in position 6 (counting from the C-terminus or array-coupled terminus), discrimination becomes more reproducible between experiments. Accordingly, it was demonstrated that placing the mutation or polymorphism closer to the array-coupled terminus provides for improved capabilities for accurately and reproducibly detecting the polymorphism.

Sensitivity

To address sensitivity, the number of mutations, defined as a mean fold difference between control signal and mutant signal threshold of 2 and a statistical significance of 0.01 (2 sample homoscedastic t-test) across probe replicates, are tabulated in Table 3 for a mutation in positions 6, 9, and 12 (counting from the C-terminus or array-coupled terminus). The overall trend is an increased ability to detect mutations when the mutation is placed in position 6 as numbered from the C-terminus (i.e., the array-coupled terminus).

TABLE 3

The number of mutations detected stratified by the mutation position

| mutation position (#'d from C-terminus) | Number of Mutations Detected | | | | | |
|---|---|---|---|---|---|---|
| | Low | med | high | control | ISD | MPS |
| 6 | 153 | 95 | 98 | 147 | 157 | 153 |
| 9 | 132 | 70 | 79 | 129 | 131 | 126 |
| 12 | 111 | 61 | 77 | 112 | 98 | 92 |

The present invention is presented in several varying embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the system. One skilled in the relevant art will recognize, however, that the system and method may both be practiced without one or more of the specific details, or with other methods, components, materials, and so forth. In other instances, well-known structures, materials, or operations are not shown or described in detail to avoid obscuring aspects of the invention. Accordingly, the foregoing description is meant to be exemplary, and does not limit the scope of present inventive concepts.

Each reference identified in the present application is herein incorporated by reference in its entirety.

What is claimed is:

1. A method of identifying a peptide antigen, the method comprising:
   a) contacting an antibody-comprising composition derived from a subject to a peptide microarray having an array surface and a plurality of feature pairs disposed thereon, each of the feature pairs including a first feature of wild-type peptides having a defined sequence and a second feature of mutant peptides having the defined sequence with a single amino acid mutation, each of the wild-type peptides and the mutant peptides having an array-coupled terminus coupled to the array surface and an opposing free terminus, the position of the amino acid mutation in the mutant peptides located closer to the array-coupled terminus of the mutant peptides than the free terminus;
   b) detecting binding of an antibody in the antibody-comprising composition to at least one of the plurality of feature pairs on the peptide microarray; and
   c) identifying feature pairs exhibiting differential binding.

2. The method of claim 1, wherein the position of the amino acid mutation in the mutant peptides is located within the first 9 amino acid positions numbered from the array-coupled terminus of the mutant peptides.

3. The method of claim 1, wherein the position of the amino acid mutation in the mutant peptides is located at amino acid position 6 numbered from the array-coupled terminus of the mutant peptides.

4. The method of claim 1, wherein the array-coupled terminus of the mutant peptides is the C-terminus.

5. The method of claim 1, wherein the single amino acid mutation is selected from one of a substitution, a modification, a deletion, and an insertion.

6. The method of claim 1, wherein each of the array-coupled termini are coupled to the array surface via at least one of a linker and a spacer.

7. The method of claim 6, wherein the spacer includes at least one amino acid selected from glycine and serine.

8. The method of claim 6, wherein the linker includes at least one 6-hexanoic acid molecule.

9. The method of claim 1, wherein each of the wild-type peptides and the mutant peptides has a length of at least 12 amino acids.

10. The method of claim 9, wherein the position of the amino acid mutation in the mutant peptides is located within the first 6 amino acids positions numbered from the array-coupled terminus of the mutant peptides.

11. The method of claim 1, wherein each of the wild-type peptides and the mutant peptides has a length of at least 16 amino acids.

12. The method of claim 1, further comprising:
d) characterizing the mutant peptides identified in step c) as neoantigens.

13. The method of claim 12, further comprising diagnosing autoimmune disease in the subject.

14. The method of claim 1, wherein the antibody-comprising composition is a blood serum composition.

15. A system for identifying a peptide antigen, the system comprising:
a peptide microarray having an array surface and a plurality of feature pairs disposed thereon, each of the feature pairs including a first feature of wild-type peptides having a defined sequence and a second feature of mutant peptides having the defined sequence with a single amino acid mutation, each of the wild-type peptides and the mutant peptides having an array-coupled terminus coupled to the array surface and an opposing free terminus, the position of the amino acid mutation in the mutant peptides located closer to the array-coupled terminus of the mutant peptides than the free terminus; and
a detector for detecting binding of an antibody in the antibody-comprising composition to at least one of the plurality of feature pairs on the peptide microarray.

16. The system of claim 15, wherein the position of the amino acid mutation in the mutant peptides is located within the first 6 amino acid positions relative to the array-coupled terminus of the mutant peptides.

17. The system of claim 15, wherein each of the array-coupled termini are coupled to the array surface via at least one of a linker and a spacer.

18. The system of claim 15, wherein each of the wild-type peptides and the mutant peptides has a length of at least 12 amino acids.

19. A peptide microarray for identifying a peptide antigen, the peptide microarray comprising:
an array surface; and
a plurality of feature pairs disposed thereon, each of the feature pairs including:
a first feature of wild-type peptides having a defined sequence, and
a second feature of mutant peptides having the defined sequence with a single amino acid mutation,
wherein each of the wild-type peptides and the mutant peptides has an array-coupled terminus coupled to the array surface and an opposing free terminus,
wherein the position of the amino acid mutation in the mutant peptides is located closer to the array-coupled terminus of the mutant peptides than the free terminus, and
wherein the each of the wild-type peptides and the mutant peptides has a length of at least 12 amino acids.

20. The peptide microarray of claim 19, wherein the position of the amino acid mutation in the mutant peptides is located within the first 6 amino acid positions relative to the array-coupled terminus of the mutant peptides.

* * * * *